(12) United States Patent
Maase

(10) Patent No.: US 7,754,053 B2
(45) Date of Patent: Jul. 13, 2010

(54) DISTILLATION OF IONIC LIQUIDS

(75) Inventor: Matthias Maase, Speyer (DE)

(73) Assignee: BASF SE, Ludwigshafen (DE)

( * ) Notice: Subject to any disclaimer, the term of this patent is extended or adjusted under 35 U.S.C. 154(b) by 907 days.

(21) Appl. No.: 10/585,868

(22) PCT Filed: Jan. 7, 2005

(86) PCT No.: PCT/EP2005/000084

§ 371 (c)(1),
(2), (4) Date: Jul. 11, 2006

(87) PCT Pub. No.: WO2005/068404

PCT Pub. Date: Jul. 28, 2005

(65) Prior Publication Data

US 2007/0095645 A1    May 3, 2007

(30) Foreign Application Priority Data

Jan. 16, 2004    (DE)    ........................ 10 2004 002 420

(51) Int. Cl.
*B01D 3/00*    (2006.01)
*C07D 233/54*    (2006.01)
*C07D 233/58*    (2006.01)

(52) U.S. Cl. ............................ 203/2; 203/98; 203/100; 548/341.1; 548/343.5; 548/345.1; 548/346.1

(58) Field of Classification Search .................. 203/2, 203/98, 100; 548/300.1, 341.1, 343.1, 343.5, 548/345.1, 347.1
See application file for complete search history.

(56) References Cited

U.S. PATENT DOCUMENTS

| 5,994,602 A | * | 11/1999 | Abdul-Sada et al. | ........ | 585/457 |
| 6,623,659 B2 | * | 9/2003 | Munson et al. | ............. | 252/184 |
| 6,774,240 B2 | * | 8/2004 | Seddon et al. | ........... | 548/347.1 |
| 6,939,974 B2 | * | 9/2005 | Earle et al. | ............... | 548/347.1 |

FOREIGN PATENT DOCUMENTS

| DE | 102 02 838 A1 | 8/2003 |
| WO | WO-2005/019183 A1 | 3/2005 |

OTHER PUBLICATIONS

Peter Wasserscheidt, Chemie in unserer Zeit 37 (2003) No. 1, pp. 52-63.
P. Dyson et al. "Transition Metal Catalysed Reactions in Room-Temperature Ionic Liquids" in *Electtrochemical Society Proceedings*, vol. 99-41, pp. 161-168.
L. Rebelo et al. "On the Critical Temperature, Normal Boiling Point, and Vapor Pressure of Ionic Liquids" *The Journal of Physical Chemistry II*, vol. 109, Mar. 12, 2005, pp. 6040-6043.
J.H. Davis et al. "Synthesis and Purification of Ionic Liquids" *Ionic Liquids in Synthesis Online*: 2002, Wiley-VCH Voley GmbH & Co KGaA: url: http://www3.interscience.wiley.com/egi-bin/booktext/102529605/bookpdfstart pp. 7-40.

* cited by examiner

*Primary Examiner*—Virginia Manoharan
(74) *Attorney, Agent, or Firm*—Connolly Bove Lodge & Hutz LLP

(57) ABSTRACT

The invention relates to a process for the distillation of ionic liquids, in which a pressure not higher than ambient pressure is set in a first step and the ionic liquid is heated to a temperature in the range from 60° C. to 350° C. in a second step. The process is employed, in particular, for the purification of ionic liquids.

18 Claims, No Drawings

DISTILLATION OF IONIC LIQUIDS

CROSS REFERENCE TO RELATED APPLICATIONS

This application is a National Phase of PCT/EP2005/000084, filed Jul. 1, 2005, which claims priority to German application no. 10 2004 002420.0, filed Jan. 16, 2004.

Description

The present invention describes a process and its use for the distillation of ionic liquids.

Ionic liquids are becoming increasingly important as solvents, e.g. in carrying out chemical reactions. Peter Wasserscheidt, Chemie in unserer Zeit 37 (2003) No. 1, pages 52-63, gives an overview of the use of ionic liquids for multiphase catalysis. It is stated by him that an advantage of the use of ionic liquids as solvents is that no solvent vaporizes because of the undetectable low vapor pressure of the ionic liquid.

When ionic liquids are used for carrying out chemical reactions, the purity of the ionic liquids used if of great important. Impurities can, for example, have a generally adverse effect on the course of chemical reactions. Thus, for example, P. Tyson et al. in Electrochemical Society Proceedings, vol. 99-41, pages 161-168, refer to problems in the use of chloride-containing ionic liquids in liquid-phase hydrogenation and in the Suzuki reaction. In the preparation of ionic liquids, therefore, the purity of the desired liquid has to meet high standards.

For the purposes of the present invention, ionic liquids are salts which are in the liquid state at low temperatures, preferably below 100° C.

It is an object of the present invention to develop an industrially useable process for purifying ionic liquids.

It has been found that cations, anions and uncharged molecules which are formed, for example, by protonation or alkylation of the anions by the cations are present in equilibrium in an ionic liquid.

In the alkylation, it is believed that a positively charged alkyl radical which is preferably bound to a heteroatom of the cation is transferred to the anion. Heteroatoms are, for example, nitrogen, oxygen, phosphorus or sulfur. Suitable alkyls are $C_1$-$C_{18}$-alkyls, preferably $C_1$-$C_{10}$-alkyls, particularly preferably $C_1$-$C_6$-alkyls, and very particular preference is given to $CH_3^+$ as positively charged alkyl radical. In contrast, protonation involves transfer of a proton from a heteroatom of the cation to the anion.

The abovementioned object of the invention is achieved by a process for the distillation of ionic liquids, in which a pressure not higher than ambient pressure is set in a first step and the ionic liquid is heated to a temperature in the range from 60° C. to 350° C. in a second step.

In a preferred variant, cations, anions and uncharged molecules which are formed, in particular, by protonation or alkylation of the anions by the cations are present in equilibrium in the ionic liquid.

In a further preferred process variant, at least the more volatile of the uncharged molecules is distilled off in the distillation.

Although ionic liquids have no measurable vapor pressure, it has been found that they can be distilled at pressures of from <1 bar, preferably <200 mbar, more preferably <50 mbar and very particularly preferably <5 mbar, and at bottom temperatures in the range from 60° C. to 350° C., preferably in the range from 100° C. to 350° C. and in particular in the range from 150° C. to 350° C.

In a preferred embodiment, the more volatile of the uncharged molecules is recovered in a targeted manner by being separated off. The molecule which has been recovered in this way can, for example, be used again later for preparing the same ionic liquid or a different ionic liquid.

In a particularly preferred embodiment, both uncharged molecules of the ionic liquid are distilled off and recombined later in a receiver to form the same ionic liquid. An ionic liquid of high purity is obtained by means of this selective removal of the uncharged molecules of the ionic liquid and their recombination in the receiver after condensation.

For the purposes of the present invention, ionic liquids are salts of the general formula

where n=1, 2, 3 or 4.

Compounds which are suitable for formation of the cation $[A]_n^+$ of ionic liquids are, for example, known from DE 102 02 838 A1. Thus, such compounds can contain oxygen, phosphorus, sulfur or, in particular, nitrogen atoms, for example at least one nitrogen atom, preferably 1-10 nitrogen atoms, particularly preferably 1-5, very particularly preferably 1-3 and in particular 1-2 nitrogen atoms. Further heteroatoms such as oxygen, sulfur or phosphorus atoms may also be present. The nitrogen atom is a suitable carrier of the positive charge in the cation of the ionic liquid from which a proton or an alkyl radical can then be transferred in equilibrium to the anion so as to produce an electrically neutral molecule.

Preference is given to compounds containing at least one five- or six-membered heterocycle which contains at least one nitrogen atom and, if desired, an oxygen or sulfur atom, particularly preferably compounds containing at least one five- or six-membered heterocycle which contains one, two or three nitrogen atoms and a sulfur or oxygen atom, very particularly preferably heterocycles having two nitrogen atoms.

Particularly preferred compounds are ones which have a molecular weight of less than 1000 g/mol, very particularly preferably less than 500 g/mol and in particular less than 250 g/mol.

Furthermore, preference is given to compounds for forming the cation which are selected from among the compounds of the formulae (Ia) to (Ir),

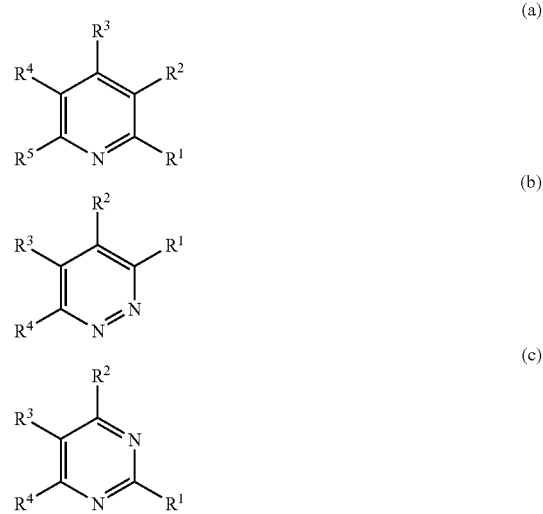

-continued

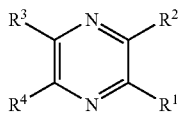 (d)

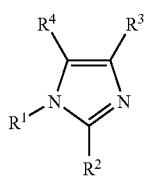 (e)

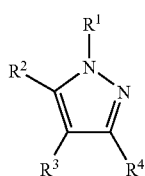 (f)

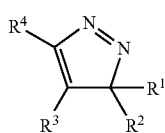 (g)

 (h)

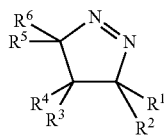 (i)

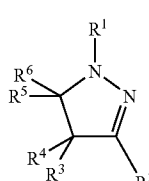 (j)

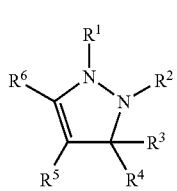 (k)

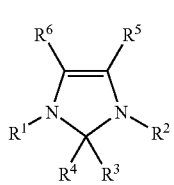 (l)

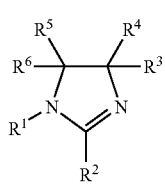 (m)

-continued (n)

(o)

(p)

(q)

(r)

and oligomers and polymers in which these structures are present, where the substituents and indices have the following meanings:

$R^1$, $R^2$, $R^3$, $R^4$, $R^5$ and $R^6$ are each, independently of one another, hydrogen, $C_1$-$C_{18}$-alkyl, $C_2$-$C_{18}$-alkyl which may be interrupted by one or more nonadjacent oxygen and/or sulfur atoms and/or one or more substituted or unsubstituted imino groups, $C_6$-$C_{14}$-aryl, $C_5$-$C_{12}$-cycloalkyl or a five- or six-membered oxygen-, nitrogen- and/or sulfur-containing heterocycle, or two of them together form an unsaturated, saturated or aromatic ring which may be interrupted by one or more nonadjacent oxygen and/or sulfur atoms and/or one or more substituted or unsubstituted imino groups, where the radicals mentioned may each be additionally substituted by functional groups, aryl, alkyl, aryloxy, alkyloxy, halogen, heteroatoms and/or heterocycles.

In these definitions, $C_1$-$C_{18}$-alkyl which may be substituted by functional groups, aryl, alkyl, aryloxy, alkyloxy, halogen, heteroatoms and/or heterocycles is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, heptadecyl, octadecyl, 1,1-dimethylpropyl, 1,1-dimethylbutyl, 1,1,3,3-tetramethylbutyl, benzyl, 1-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di-(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl.

$C_2$-$C_{18}$-Alkyl which may be interrupted by one or more nonadjacent oxygen and/or sulfur atoms and/or one or more substituted or unsubstituted imino groups is, for example, 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxapentadecyl, 9-hydroxy-5-oxanonyl, 14-hydroxy-5,10-oxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

If two radicals form a ring, they can together form as fused-on building block, for example, 1,3-propylene, 1,4-butylene, 2-oxa-1,3-propylene, 1-oxa-1,3-propylene, 2-oxa-1,3-propenylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The number of nonadjacent oxygen and/or sulfur atoms and/or imino groups is in principle not restricted or is restricted automatically by the size of the radical or of the ring building block. In general, there will be no more than 5 in the respective radical, preferably no more than 4 and very particularly preferably no more than 3. Furthermore, there is generally at least one carbon atom, preferably at least two carbon atoms, between any two heteroatoms.

Substituted and unsubstituted imino groups can be, for example, imino, methylimino, isopropylimino, n-butylimino or tert-butylimino.

The term "functional groups" refers, for example, to the following groups: carboxy, carboxamide, hydroxy, di($C_1$-$C_4$-alkyl)amino, $C_1$-$C_4$-alkyloxycarbonyl, cyano or $C_1$-$C_4$-alkoxy. Here, $C_1$-$C_4$-alkyl is methyl, ethyl, propyl, isopropyl, n-butyl, sec-butyl or tert-butyl.

$C_6$-$C_{14}$-Aryl which may be substituted by functional groups, aryl, alkyl, aryloxy, alkyloxy, halogen, heteroatoms and/or heterocycles is, for example, phenyl, tolyl, xylyl, α-naphthyl, β-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethyl-phenyl.

$C_5$-$C_{12}$-Cycloalkyl which may be substituted by functional groups, aryl, alkyl, aryloxy, halogen, heteroatoms and/or heterocycles is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl or a saturated or unsaturated bicyclic system such as norbornyl or norbornenyl.

A five- or six-membered, oxygen-, nitrogen- and/or sulfur-containing heterocycle is, for example, furyl, thiophenyl, pyrryl, pyridyl, indolyl, benzoxazolyl, dioxolyl, dioxyl, benzimidazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl.

Preference is given to $R^1$, $R^2$, $R^3$, $R^4$, $R^5$ and $R^6$ each being, independently of one another, hydrogen, methyl, ethyl, n-butyl, 2-hydroxyethyl, 2-cyanoethyl, 2-(methoxycarbonyl)ethyl, 2-(ethoxycarbonyl)ethyl, 2-(n-butoxycarbonyl)ethyl, dimethylamino, diethylamino or chlorine.

Particularly preferred pyridines (Ia) are those in which one of the radicals $R^1$ to $R^5$ is methyl, ethyl or chlorine and all others are hydrogen, or $R^3$ is dimethylamino and all others are hydrogen, or all the radicals are hydrogen, or $R^2$ is carboxy or carboxamide and all others are hydrogen, or $R^1$ and $R^2$ or $R^2$ and $R^3$ are together 1,4-buta-1,3-dienylene and all others are hydrogen.

Particularly preferred pyridazines (Ib) are those in which one of the radicals $R^1$ to $R^4$ is methyl or ethyl and all others are hydrogen or all the radicals are hydrogen.

Particularly preferred pyrimidines (Ic) are those in which $R^2$ to $R^4$ are each hydrogen or methyl and $R^1$ is hydrogen, methyl or ethyl, or $R^2$ and $R^4$ are each methyl, $R^3$ is hydrogen and $R^1$ is hydrogen, methyl or ethyl.

Particularly preferred pyrazines (Id) are those in which $R^1$ to $R^4$ are all methyl or all hydrogen.

Particularly preferred imidazoles (Ie) are those in which, independently of one another, $R^1$ is selected from among methyl, ethyl, n-propyl, n-butyl, n-pentyl, n-octyl, 2-hydroxyethyl and 2-cyanoethyl, and $R^2$ to $R^4$ are each, independently of one another, hydrogen, methyl or ethyl.

Particularly preferred 1H-pyrazoles (If) are those in which, independently of one another, $R^1$ is selected from among hydrogen, methyl or ethyl, and $R^2$, $R^3$ and $R^4$ are selected from among hydrogen and methyl.

Particularly preferred 3H-pyrazoles (Ig) are those in which, independently of one another, $R^1$ is selected from among hydrogen, methyl and ethyl, and $R^2$, $R^3$ and $R^4$ are selected from among hydrogen and methyl.

Particularly preferred 4H-pyrazoles (Ih) are those in which, independently of one another, $R^1$ to $R^4$ are selected from among hydrogen and methyl.

Particularly preferred 1-pyrazolines (Ii) are those in which, independently of one another, $R^1$ to $R^6$ are selected from among hydrogen and methyl.

Particularly preferred 2-pyrazolines (Ij) are those in which, independently of one another, $R^1$ is selected from among hydrogen, methyl, ethyl and phenyl, and $R^2$ to $R^6$ are selected from among hydrogen and methyl.

Particularly preferred 3-pyrazolines (Ik) are those in which, independently of one another, $R^1$ and $R^2$ are selected from among hydrogen, methyl, ethyl or phenyl and $R^3$ to $R^6$ are selected from among hydrogen and methyl.

Particularly preferred imidazolines (Il) are those in which, independently of one another, $R^1$ and $R^2$ are selected from among hydrogen, methyl, ethyl, n-butyl and phenyl, and $R^3$ and $R^4$ are selected from among hydrogen, methyl and ethyl, and $R^5$ and $R^6$ are selected from among hydrogen and methyl.

Particularly preferred imidazolines (Im) are those in which, independently of one another, $R^1$ and $R^2$ are selected from among hydrogen, methyl and ethyl, and $R^3$ to $R^6$ are selected from among hydrogen and methyl.

Particularly preferred imidazolines (In) are those in which, independently of one another, $R^1$, $R^2$ and $R^3$ are selected from among hydrogen, methyl and ethyl, and $R^4$ to $R^6$ are selected from among hydrogen and methyl.

Particularly preferred thiazoles (Io) or oxazoles (Ip) are those in which, independently of one another, $R^1$ is selected from among hydrogen, methyl, ethyl and phenyl, and $R^2$ and $R^3$ are selected from among hydrogen and methyl.

Particularly preferred 1,2,4-triazoles (Iq) are those in which, independently of one another, $R^1$ and $R^2$ are selected from among hydrogen, methyl, ethyl and phenyl, and $R^3$ is selected from among hydrogen, methyl and phenyl.

Particularly preferred 1,2,3-triazoles (Ir) are those in which, independently of one another, $R^1$ is selected from among hydrogen, methyl and ethyl and $R^2$ and $R^3$ are selected from among hydrogen and methyl, or $R^2$ and $R^3$ are together 1,4-buta-1,3-dienylene and all others are hydrogen.

Among the abovementioned heterocycles, the pyridines and the imidazoles are preferred.

Very particularly preferred compounds for formation of the cation are 3-chloropyridine, 4-dimethylaminopyridine, 2-ethyl-4-aminopyridine, 2-methylpyridine, 2-ethylpyridine, 2-ethyl-6-methylpyridine, quinoline, isoquinoline, pyridine, 1-$C_1$-$C_4$-alkylimidazole, 1-methylimidazole, 1,2-dimethylimidazole, 1-n-butylimidazole, 1,4,5-trimethylimidazole, 1,4-dimethylimidazole, imidazole, 2-methylimidazole, 1-butyl-2-methylimidazole, 4-methylimidazole, 1-n-pentylimidazole, 1-n-hexylimidazole, 1-n-octylimidazole, 1-(2'-aminoethyl)imidazole, 2-ethyl-4-methylimidazole, 1-vinylimidazole, 2-ethylimidazole, 1-(2'-cyanoethyl)imidazole and benzotriazole. A special preference is given to 1-n-butylimidazole, 1-methylimidazole, 2-methylpyridine and 2-ethylpyridine.

Also suitable are tertiary amines of the formula (Il)

$$NR^aR^bR^c \qquad (Il)$$

where $R^a$, $R^b$ and $R^c$ are each, independently of one another, $C_1$-$C_{18}$-alkyl, $C_2$-$C_{18}$-alkyl which may be interrupted by one or more nonadjacent oxygen and/or sulfur atoms and/or one or more substituted or unsubstituted imino groups, $C_6$-$C_{14}$-aryl, $C_5$-$C_{12}$-cycloalkyl or a five- or six-membered oxygen-, nitrogen- and/or sulfur-containing heterocycle, or two of them which together form an unsaturated, saturated or aromatic ring which may be interrupted by one or more nonadjacent oxygen and/or sulfur atoms and/or one or more substituted or unsubstituted imino groups, where the radicals mentioned may each be additionally substituted by functional groups, aryl, alkyl, aryloxy, alkyloxy, halogen, heteroatoms and/or heterocycles, with the proviso that at least two of the three radicals $R^a$, $R^b$ and $R^c$ are different and the radicals $R^a$, $R^b$ and $R^c$ together have at least 8, preferably at least 10, particularly preferably at least 12 and very particularly preferably at least 13, carbon atoms.

Preference is given to $R^a$, $R^b$ and $R^c$ each being, independently of one another, $C_1$-$C_{18}$-alkyl, $C_6$-$C_{12}$-aryl or $C_5$-$C_{12}$-cycloalkyl, particularly preferably $C_1$-$C_{18}$-alkyl, where the radicals mentioned may each be substituted by functional groups, aryl, alkyl, aryloxy, alkyloxy, halogen, heteroatoms and/or heterocycles.

Examples of the respective groups have been given above.

The radicals $R^a$, $R^b$ and $R^c$ are preferably methyl, ethyl, n-propyl, isopropyl, n-butyl, sec-butyl, tert-butyl, n-pentyl(n-amyl), 2-pentyl(sec-amyl), 3-pentyl, 2,2-dimethylprop-1-yl (neopentyl), n-hexyl, n-heptyl, n-octyl, isooctyl, 2-ethylhexyl, 1,1-dimethyl-propyl, 1,1-dimethylbutyl, benzyl, 1-phenylethyl, 2-phenylethyl, α,α-dimethylbenzyl, phenyl, tolyl, xylyl, α-naphthyl, β-naphthyl, cyclopentyl or cyclohexyl.

If two radicals $R^a$, $R^b$ and $R^c$ form a chain, this can be, for example, 1,4-butylene or 1,5-pentylene.

Examples of tertiary amines of the formula (Il) are diethyl-n-butylamine, diethyl-tert-butylamine, diethyl-n-pentylamine, diethylhexylamine, diethyloctylamine, diethyl(2-ethylhexyl)amine, di-n-propylbutylamine, di-n-propyl-n-pentylamine, di-n-propylhexylamine, di-n-propyloctylamine, di-n-propyl(2-ethylhexyl)amine, diisopropylethylamine, diisopropyl-n-propylamine, diisopropylbutylamine, diisopropylpentylamine, diisopropylhexylamine, diisopropyloctylamine, diisopropyl(2-ethylhexyl)amine, di-n-butylethylamine, di-n-butyl-n-propylamine, di-n-butyl-n-pentylamine, di-n-butylhexylamine, di-n-butyloctylamine, di-n-butyl(2-ethylhexyl)amine, N-n-butylpyrrolidine, N-sec-butylpyrrolidine, N-tert-butylpyrrolidine, N-n-pentylpyrrolidine, N,N-dimethylcyclohexylamine, N,N-diethylcyclohexylamine, N,N-di-n-butylcyclohexylamine, N-n-propylpiperidine, N-isopropylpiperidine, N-n-butylpiperidine, N-sec-butylpiperidine, N-tert-butylpiperidine, N-n-pentylpiperidine, N-n-butylmorpholine, N-sec-butylmorpholine, N-tert-butylmorpholine, N-n-pentylmorpholine, N-benzyl-N-ethylaniline, N-benzyl-N-n-propylaniline, N-benzyl-N-isopropylaniline, N-benzyl-N-n-butylaniline, N,N-dimethyl-p-toluidine, N,N-diethyl-p-toluidine, N,N-di-n-butyl-p-toluidine, diethylbenzylamine, di-n-propylbenzylamine, di-n-butylbenzylamine, diethyphenylamine, di-n-propylphenylamine and di-n-butylphenylamine.

Preferred tertiary amines (Il) are diisopropylethylamine, diethyl-tert-butylamine, diisopropylbutylamine, di-n-butyl-n-pentylamine, N,N-di-n-butylcyclohexylamine and also tertiary amines derived from pentyl isomers.

Particularly preferred tertiary amines are di-n-butyl-n-pentylamine and tertiary amines derived from pentyl isomers.

One tertiary amine which is likewise preferred and can be used according to the invention but in contrast to those listed above has three identical radicals is triallylamine.

Anions [Y]$^{n-}$ of the ionic liquid are, for example, fluoride, chloride, bromide, iodide, nitrate, nitrite, carbonate, hydrogencarbonate, sulfate, hydrogensulfate, sulfite, hydrogensulfite, phosphate, hydrogenphosphate, dihydrogenphosphate, borate, hydrogenborate, dihydrogenborate, tetrafluoroborate, tetrachloroborate, hexafluorophosphate, hexafluoroantimonate, hexafluoroarsenate, fluorosulfonate, dichlorocuprate, trichlorozincate, tetrabromoaluminate and chloroaluminates ($AlCl_4^-$, $Al_2Cl_7^-$, $Al_3Cl_{10}^-$).

Preference is also given to anions selected from among
$R^1$—COO$^-$, $R^1$—OCOO$^-$, $R^1$—SO$_3^-$, $R^1$—OSO$_3^-$, 
$R^1$—PO$_4^{2-}$, $R^1$—$R^2$—PO$_4^-$, $R^1$—BO$_3^{2-}$, $R^1$—$R^2$—BO$_3^-$, B(OR$^1$)(OR$^2$)(OR$^3$)(OR$^4$)$^-$, (R$^1$—SO$_2$)$_2$N$^-$.

In these formulae, $R^1$, $R^2$, $R^3$ and $R^4$ are each, independently of one another, hydrogen, $C_1$-$C_{18}$-alkyl which may be interrupted by one or more nonadjacent oxygen and/or sulfur atoms and/or one or more substituted or unsubstituted imino groups, $C_6$-$C_{14}$-aryl, $C_5$-$C_{12}$-cycloalkyl, where the radicals mentioned may each be additionally substituted by functional groups, aryl, alkyl, aryloxy, alkyloxy, halogen, heteroatoms and/or heterocycles.

Here, $C_1$-$C_{18}$-alkyl which may be substituted by functional groups, aryl, alkyl, aryloxy, alkyloxy, halogen, heteroatoms and/or heterocycles is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, heptadecyl, octadecyl, 1,1-dimethyl-propyl, 1,1-dimethylbutyl, 1,1,3,3-tetramethylbutyl, benzyl, 1-phenyl-ethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl.

$C_2$-$C_{18}$-Alkyl which may be interrupted by one or more nonadjacent oxygen and/or sulfur atoms and/or one or more substituted or unsubstituted imino groups is, for example, 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxapentadecyl, 9-hydroxy-5-oxanonyl, 14-hydroxy-5,10-oxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

If two radicals form a ring, they can together form as fused-on building block, for example, 1,3-propylene, 1,4-butylene, 2-oxa-1,3-propylene, 1-oxa-1,3-propylene, 2-oxa-1,3-propenylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The number of nonadjacent oxygen and/or sulfur atoms and/or imino groups is in principle not restricted or is restricted automatically by the size of the radical or of the ring building block. In general, there will be no more than 5 in the respective radical, preferably no more than 4 and very particularly preferably no more than 3. Furthermore, there is generally at least one carbon atom, preferably at least two carbon atoms, between any two heteroatoms.

Substituted and unsubstituted imino groups can be, for example, imino, methylimino, isopropylimino, n-butylimino or tert-butylimino.

The term "functional groups" refers, for example, to the following groups: carboxy, carboxamide, hydroxy, di($C_1$-$C_4$-alkyl)amino, $C_1$-$C_4$-alkyloxycarbonyl, cyano or $C_1$-$C_4$-alkoxy. Here, $C_1$-$C_4$-alkyl is methyl, ethyl, propyl, isopropyl, n-butyl, sec-butyl or tert-butyl.

$C_6$-$C_{14}$-Aryl which may be substituted by functional groups, aryl, alkyl, aryloxy, alkyloxy, halogen, heteroatoms and/or heterocycles is, for example, phenyl, tolyl, xylyl, α-naphthyl, β-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl.

$C_5$-$C_{12}$-Cycloalkyl which may be substituted by functional groups, aryl, alkyl, aryloxy, halogen, heteroatoms and/or heterocycles is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl or a saturated or unsaturated bicyclic system such as norbornyl or norbornenyl.

Both cations and anions are present in the ionic liquid. Within the ionic liquid, a proton or an alkyl radical is transferred from the cation to the anion. This results in formation of two uncharged molecules. The result is an equilibrium in which anions, cations and the two uncharged molecules are present.

The uncharged molecules present in equilibrium in the ionic liquid can be distilled from the ionic liquid. This influences the equilibrium within the ionic liquid. As a result, anions are once again protonated or alkylated by the cations in order to reestablish the equilibrium. This mechanism leads to the ionic liquid being able to be distilled.

In a preferred embodiment, the molecules which have been distilled off are condensed and collected in a receiver. Heating converts the condensate back into an ionic liquid.

The ionic liquid or component of the liquid obtained by distillation is advantageously free of impurities.

If one of the molecules distilled off is high-volatile, it may not condense in the receiver. This makes it possible to recover only one of the components selectively. This can also be deliberately controlled in a targeted manner by means of appropriate temperature control and/or pressure control in the distillation or the condensation in the receiver. The component which has been recovered in this way is likewise present in high purity and can later be reused for preparing an ionic liquid.

The distillation of the ionic liquids makes it possible to purify them or recycle them. There is also the possibility of recovering the components of the anion or of the cation from the ionic liquid in uncharged form.

In the distillation of small amounts of ionic liquid, the distillation is preferably carried out from a glass flask via a distillation attachment. In particular, one of the typical distillation apparatuses as is known from the laboratory to a person skilled in the art is suitable.

In a batch distillation, the ionic liquid can be placed in a distillation pot, heated to boiling point in this and partly vaporized. The uncharged molecules which vaporize from the anionic liquid are taken off from the distillation pot, condensed then cooled in a condenser and collected in a distillate receiver. In the distillate receiver, the molecules which have been separated off can, if both types of components go over, recombine to form the ionic liquid.

To distill an ionic liquid continuously, it is preferably added as liquid to the bottom of a distillation column. Vaporizing components are preferably taken off via the top of the column. The components taken off via the top are then preferably condensed in a heat exchanger and preferably collected in a receiver.

The distillation apparatuses used for distillation of the ionic liquids are preferably sealed from the environment so that, for example, a vacuum can be generated in the distillation apparatus.

The liquid phase can be heated, for example, electrically or by means of a heating medium. Suitable heating media are, for example, steam, heat transfer fluids or salt melts.

EXAMPLES

Example 1

Distillation of EMIM Cl

A 250 ml glass flask is charged with the ionic liquid EMIM Cl. Here, EMIM is a mixture of 1-methylimidazole and 1-ethylimidazole. At a pressure of 2.4 mbar, the liquid distills off completely via a distillation attachment at a transition temperature of 59° C. The temperature at the bottom is 215° C. The methyl chloride or ethyl chloride formed in the distillation is not condensed. The distillate is examined by means of $^1$H NMR spectroscopy. It contains exclusively 1-methylimidazole and 1-ethylimidazole in a ratio of 1:2.7.

Example 2

Distillation of EMIM Diethyl Phosphate 62 g of EMIM diethyl phosphate are placed in a distillation apparatus. At a pressure of 0.2 mbar, a yellow-orange liquid distills off at a transition temperature of 54° C. The temperature at the bottom during the distillation is 223° C. Analysis of the distillate by means of $^1$H NMR spectroscopy shows that the distillate consists of a mixture of 1-methylimidazole, 1-ethylimidazole and triethyl phosphate.

Example 3

Distillation of EMIM Diethyl Phosphate without Reduced Pressure 90 g of EMIM diethyl phosphate are placed in a distillation apparatus. A colorless distillate distills off at a temperature at the bottom of 254° C. and a transition temperature of 78° C.

Example 4

Preparation and Distillation of HMIM Cl 821.2 g (10 mol) of 1-methylimidazole are placed in a reaction flask. 985.4 g (10 mol) of 37% strength aqueous HCl are added dropwise to the 1-methylimidazole until the mixture begins to boil. 65.6 g of water are firstly distilled off at a pressure of 40 mbar and 37° C. 1032 g of a liquid are subsequently distilled off at a pressure of 0.2-0.5 mbar, a temperature at the bottom of 200° C. and a transition temperature of 145° C.-159° C. After cooling, this liquid solidifies to give a colorless solid. Analysis of the solid by means of 1H NMR spectroscopy shows that the solid is pure HMIM Cl (methylimidazole chloride). Elemental analysis of the distillate shows that the distillate contains 29.5% of chloride.

Example 5

Preparation, Distillation and Recombination of MMIM Dimethyl Phosphate 70.0 g (0.5 mol) of trimethyl phosphate are added dropwise to 41.1 g (0.5 mol) of N-methylimidazole at 85° C. As a result of the exothermic reaction, the temperature rises to 102° C. Stirring is continued for another 3 hours at 95° C. 111 g of the ionic liquid MMIM dimethyl phosphate are obtained. The $^1$H NMR spectrum (CDCl$_3$) shows the corresponding signals at 10.5 ppm (1H, N—CH—N), 7.6 ppm (2H, N—CH—CH—N), 4.0 ppm (6H, N—CH$_3$) and a doublet at 3.6 ppm (6H, POCH$_3$).

The MMIM dimethyl phosphate was distilled off at 0.1 mbar, a temperature at the bottom of 110-196° C. and a temperature at the top of 23-25° C. This gave 68.6 g of distillate whose $^1$H NMR spectrum (CDCl$_3$) shows the signals of free N-methylimidazole at 7.4 ppm (1H, N—CH—N), 7.0 ppm (1H, N—CH—CH—N), 6.9 ppm (1H, N—CH—CH—N), 3.7 ppm (3H, N—CH$_3$) and free trimethyl phosphate at 3.8 ppm (9H, POCH$_3$).

The distillate consisting of N-methylimidazole and trimethyl phosphate was heated for 5 hours at 100° C. and at atmospheric pressure. The $^1$H NMR spectrum (CDCl$_3$) of the material obtained shows the signals of the ionic liquid MMIM dimethyl phosphate at 10.3 ppm (1H, N—CH—N), 7.7 ppm (2H, N—CH—CH—N), 4.0 ppm (6H, N—CH$_3$) and the doublet at 3.6 ppm (6H, POCH$_3$).

The invention claimed is:

1. A process for a distillation of an ionic liquid, which comprises the following steps:
   setting a pressure which is not higher than ambient pressure, and
   heating to a temperature from 60° C. to 350° C., wherein cations, anions and uncharged
   molecules are present in equilibrium in the ionic liquid.

2. The process according to claim 1, wherein the cations, anions and uncharged molecules are formed by protonation or alkylation of the anions by the cations.

3. The process according to claim 2, wherein the pressure is less than 50 mbar.

4. The process according to claim 2, wherein the more volatile of the uncharged molecules is distilled off to prepare a distilled ionic liquid.

5. The process according to claim 1, wherein the pressure is less than 200 mbar.

6. The process according to claim 1, wherein the pressure is less than 50 mbar.

7. The process according to claim 1, wherein the pressure is less than 5 mbar.

8. The process according to claim 1, wherein the temperature is from 100° C. to 350° C.

9. The process according to claim 1, wherein the temperature is from 150 to 350° C.

10. The process according to claim 1, wherein two uncharged molecules are formed in the process, and the two uncharged molecules are distilled off.

11. The process according to claim 10, wherein the two uncharged molecules which have been distilled off are recombined again to form a distilled ionic liquid.

12. The process according to claim 10, wherein one of the two uncharged molecules which have been distilled off is used to prepare a distilled ionic liquid.

13. The process according to claim 1, used for a purification of the ionic liquid.

14. The process according to claim 1, used for a recirculation of the ionic liquid.

15. The process according to claim 1, wherein the uncharged molecules are formed by protonation or alkylation of the anions by the cations.

16. The process according to claim 15, wherein the more volatile molecule of the uncharged molecules is distilled off and is used to prepare a distilled ionic liquid.

17. The process according to claim 16, wherein the pressure is less than 50 mbar and the temperature is from 100° C. to 350° C.

18. The process according to claim 1, wherein the uncharged molecules are formed in the process and at least the more volatile of the uncharged molecules are distilled off.

* * * * *